(12) United States Patent
Terpin et al.

(10) Patent No.: US 9,492,602 B2
(45) Date of Patent: Nov. 15, 2016

(54) CONCENTRATE FOR A DIALYSIS LIQUID AND DIALYSIS LIQUID MADE FROM IT

(71) Applicant: FRESENIUS MEDICAL CARE DEUTSCHLAND GMBH, Bad Homburg (DE)

(72) Inventors: Andreas Terpin, Frankfurt am Main (DE); Volker Nier, Reichelsheim (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 220 days.

(21) Appl. No.: 13/761,245

(22) Filed: Feb. 7, 2013

(65) Prior Publication Data

US 2013/0240441 A1 Sep. 19, 2013

Related U.S. Application Data

(60) Provisional application No. 61/596,271, filed on Feb. 8, 2012.

(30) Foreign Application Priority Data

Feb. 8, 2012 (DE) .......................... 10 2012 002 372

(51) Int. Cl.
*A61K 9/00* (2006.01)
*A61K 9/08* (2006.01)
*A61K 9/14* (2006.01)
*A61M 1/14* (2006.01)
*A61M 1/16* (2006.01)
*A61K 45/06* (2006.01)
*A61K 31/19* (2006.01)
*A61K 33/00* (2006.01)
*A61K 33/06* (2006.01)
*A61K 33/14* (2006.01)
*A61K 33/42* (2006.01)
*A61K 47/32* (2006.01)

(52) U.S. Cl.
CPC .............. *A61M 1/1654* (2013.01); *A61K 9/08* (2013.01); *A61K 31/19* (2013.01); *A61K 33/00* (2013.01); *A61K 33/06* (2013.01); *A61K 33/14* (2013.01); *A61K 33/42* (2013.01); *A61K 45/06* (2013.01); *A61K 47/32* (2013.01); *A61M 1/14* (2013.01); *A61M 1/1666* (2014.02)

(58) Field of Classification Search
CPC .................................................. A61M 1/1666
See application file for complete search history.

(56) References Cited

U.S. PATENT DOCUMENTS

| | | | |
|---|---|---|---|
| 3,669,878 A | 6/1972 | Marantz et al. | |
| 3,874,907 A | 4/1975 | Gardon et al. | |
| 6,348,162 B1 | 2/2002 | Ash | |
| 2004/0019312 A1* | 1/2004 | Childers et al. | 604/4.01 |
| 2006/0115395 A1* | 6/2006 | Taylor | 422/261 |
| 2011/0017665 A1* | 1/2011 | Updyke et al. | 210/638 |

FOREIGN PATENT DOCUMENTS

| | | |
|---|---|---|
| DE | 2512212 A1 | 9/1975 |
| DE | 3110128 A1 | 9/1982 |
| EP | 0046971 A1 | 3/1982 |
| EP | 0064393 A2 | 11/1982 |
| GB | 1267105 A | 3/1972 |
| GB | 1484642 A | 9/1977 |
| GB | 2417420 A | 3/2006 |
| WO | WO-9011348 A1 | 10/1990 |
| WO | WO-00/51704 A1 | 9/2000 |
| WO | WO-00/57935 A1 | 10/2000 |
| WO | WO-2007/016377 A2 | 2/2007 |

OTHER PUBLICATIONS

IRN 150 MSDS.pdf; Jul. 22, 1991, Rohm and Haas.*
International Preliminary Report on Patentability, PCT/EP2013/000388, English Translation, 9 pages (Aug. 12, 2014).
International Search Report for PCT/EP2013/000388, 3 pages (May 31, 2013).
Written Opinion for PCT/EP2013/000388, English Translation, 8 pages (May 31, 2013).

* cited by examiner

*Primary Examiner* — Krishnan S Menon
*Assistant Examiner* — Bradley R Spies
(74) *Attorney, Agent, or Firm* — Choate, Hall & Stewart LLP; William R. Haulbrook; John J. Cahill

(57) ABSTRACT

Concentrate for a dialysis liquid, at least comprising one acid and one physiologically acceptable electrolyte, characterized in that the acid comprises at least one acidic ion exchanger or is an acidic ion exchanger.

7 Claims, No Drawings

CONCENTRATE FOR A DIALYSIS LIQUID AND DIALYSIS LIQUID MADE FROM IT

CROSS REFERENCE TO RELATED APPLICATIONS

This application claims the benefit of, and priority to, U.S. Provisional Application No. 61/596,271, filed Feb. 8, 2012, and German Application No. 10 2012 002 372.3, filed Feb. 8, 2012, each of which is hereby incorporated by reference in its entirety for all purposes as if fully set forth herein.

The present invention relates to a concentrate for a dialysis liquid and to a dialysis liquid, which is made from the concentrate, and which may be used for purifying blood. The invention further relates to a method of making a dialysis liquid, to the use of the method for purifying blood and to a dialysis device, which comprises the concentrate or the dialysis liquid.

It is generally known that the blood purification by means of hemodialysis is performed according to the principle of the concentration compensation of substances having a low molecular weight, wherein said substances are present in two liquids, which are separated from one another by means of a semi-permeable membrane. The blood to be purified, which contains toxins, electrolytes as well as urine-containing substances such as urea and uric acid, is located on one side of the membrane. The dialysis liquid, which should receive the substances to be separated from the blood, is located on the other side of the membrane. The semi-permeable membrane has pores through which the small molecules such as water, electrolyte and urine-containing substances may permeate, however, which withhold large molecules such as proteins and blood cells.

The dialysate flow, i.e. the flow of the dialysis liquid, typically is approximately 0.5 l/min. Accordingly, for an average dialysis time of four to five hours, 120 l to 150 l of dialysis liquid are necessary. In general, this amount is not stored but is made by mixing and diluting a basic and an acidic concentrate with water, wherein the mixing and diluting normally is performed in the dialysis device. With this, also the pH value of the dialysis liquid may be adjusted. Additionally, physiologically acceptable electrolytes and, depending on the treatment requirement, optionally sugars such as glucose may be admixed to the dialysis liquid in the dialysis device.

Basic concentrates for dialysis solutions in general mainly consist of sodium bicarbonate, and are delivered mostly in dry form, the so-called dry concentrates. Acidic concentrates are frequently delivered in liquid form, since the selection of physiologically acceptable acids, which are provided in solid form, is limited. Mostly, hydrochloric acid or acetic acid are used in liquid acid concentrates, since in a respective dilution the respective anions are unproblematic with respect to tolerability.

The use of liquid concentrates requires that in addition to the electrolytes, which are used for the dialysis liquid, significant amounts of water have to be transported and stored. This is unfavorable for personnel and logistic.

Liquid acid concentrates, which are combined with a bicarbonate buffer, and the use thereof in hemodialysis, are described, for example, in EP 0 457 960 A2.

Acid concentrates in solid form are known from U.S. Pat. No. 5,252,213. For this, basically citric acid is used as solid acid. However, it is also known that citric acid can be used in a limited concentration range only since it may affect coagulation of blood. It is further known that acids may interact with glucose, which is contained in many dialysis liquids, which may result in a lower durability of respective dry concentrates.

One object of the present invention is the provision of improved acid concentrates, preferably in form of dry concentrates, for the manufacture of a dialysis liquid for purifying blood.

This object is achieved thereby that an acidic ion exchanger is used as acid in the concentrate for a dialysis liquid, preferably a dry concentrate, and in the dialysis liquid.

In particular the use of a dry concentrate according to the invention in the dialysis of blood allows for an operation, which is favorable for personnel and logistic. Furthermore, the dry concentrates according to the invention are characterized by a good storage stability and durability.

According to a first aspect, the present invention relates to a concentrate for a dialysis liquid, preferably a dry concentrate, comprising at least one acid and a physiologically acceptable electrolyte, which is characterized in that the acid comprises at least one acidic ion exchanger, or which is characterized in that the acid is an acidic ion-exchanger.

In one embodiment, the present invention relates to a concentrate for a dialysis liquid, preferably a dry concentrate, which consists of an acid and a physiologically acceptable electrolyte, which is characterized in that the acid comprises at least one acidic ion-exchanger, or which is characterized in that the acid is an acidic ion exchanger.

This acidic ion exchanger may release protons due to the influence of water and/or of salts, whose cations may be bound by the groups, which are present in the ion exchanger. By means of this, the pH value of the dialysis liquid may be controlled and may be adjusted.

In one embodiment, the acidic ion exchanger may be used in combination with the acids, which are typically used in dialysis, thus, for example, may be combined with citric acid or hydrochloric acid or acetic acid.

In a preferred embodiment, the acid, which is used in the concentrate, is at least one acidic ion exchanger, thus consists of the at least one ion exchanger.

The term "acidic ion exchanger" as used in this disclosure, comprises all substances, which have acidic groups, and in which protons may be substituted by means of ion exchange.

Various types of acidic ion exchangers may be used according to the invention. In one embodiment, the acidic ion exchanger is present as cation exchanger. In another embodiment, the cation exchanger comprises cross-linked synthetic resins, preferably based on cross-linked polymers or based on cellulose, which are functionalized with anionic groups, so-called cationic-active groups.

Examples of cross-linked and ion exchanging polymers are copolymers derived from styrene, and where applicable, styrene combined with further monomers that are copolymerizable with styrene, and at least one cross-linker, such as preferably divinylbenzene, in which at least a portion of the benzene cores is functionalized with cationic-active groups. Further examples of cross-linked and ion exchanging polymers are cross-linked poly(meth)acrylic acids, which may be obtained by means of copolymerization of vinylbenzene with esters of (meth)acrylic acid, and subsequent saponification.

Besides polymers, also polycondensates may be used as ion exchangers within the meaning of the invention. Examples are aminoplasts or phenol-formaldehyde resins, in which at least a part of the benzene cores has been functionalized with cationic-active groups.

Thus, the term "acidic ion exchanger" comprises all macroporous resins based on polymers or polycondensates, which have been functionalized with cationic-active groups, which may be protonated.

As acidic ion-exchangers in the meaning of the present invention, also inorganic cation exchangers may be used. Examples for this are zeolites, montmorillonites, attapulgites or bentonites.

The ion exchangers may be provided in any form. Preferably, ion exchangers are used in solid form, preferably in grained form or in powder form.

The ion exchangers may also be used in the form of ion exchanger membranes.

The ion exchangers, which are used according to the invention, are known from the prior art, or may be produced according to known methods.

In one embodiment, the acidic ion exchanger comprises protonated and/or protonable groups selected from sulfonate groups, sulfate groups, phosphate groups, phosphonate groups, carboxylate groups, or from two or more thereof. In one embodiment, said groups are bound to a cross-linked polymer, preferably bound to cross-linked polystyrene.

The term "physiologically acceptable electrolyte" as used herein, comprises all electrolytes, which do not cause intolerances or adverse effects in and at the patients during dialysis.

In one embodiment, a physiologically acceptable electrolyte has cations selected from the cations of magnesium, calcium, potassium, sodium, or from mixtures of two or more thereof. Preferably, then the anions are selected from chloride, acetate, lactate, or two or more of these anions.

In one embodiment, as physiologically acceptable electrolyte, salts are used selected from: sodium chloride, calcium chloride, magnesium chloride, sodium lactate, calcium lactate, magnesium lactate, sodium acetate, calcium acetate, magnesium acetate, or from combinations of two or more thereof.

In a further embodiment, the concentrate for the dialysis liquid contains sodium chloride. This has the advantage that under the influence of water on the ion exchanger and on the sodium salt, sodium ions get into the acidic ion exchanger, and may replace protons from the acidic ion exchanger. With this, the pH value of the dialysis liquid, which is made from the concentrate, may be targetedly adjusted.

Thus, in one embodiment, the concentrate according to the invention comprises at least one acidic ion exchanger and a physiologically acceptable electrolyte, wherein the physiologically acceptable electrolyte comprises sodium chloride or consists of sodium chloride; or the concentrate according to the invention consists of at least one acidic ion exchanger and a physiologically acceptable electrolyte, wherein the physiologically acceptable electrolyte comprises sodium chloride or consists of sodium chloride.

In a preferred embodiment, the concentrate is a dry concentrate.

The term "dry concentrate" as used herein means that in the concentrate, if at all, only minor amounts of water are present. Preferably, the water amount is less than 10 wt.-%, further preferred less than 5 wt.-%, based on the total amount of concentrate.

The resulting dry concentrate may be provided in a one-piece form or in a multi-part form, for example in a two-part form or in a three-part form.

In one embodiment, the concentrate that preferably is in the form of a dry concentrate, is in a one-piece form. In this embodiment, the concentrate comprises one component or consists of one component. The term "component" as used herein means an ingredient of the concentrate. In a one-piece form, the acidic ion exchanger and the physiologically acceptable electrolyte as well as further components of the concentrate, preferably sodium chloride, provided this is not contained in the physiologically acceptable electrolyte, may be provided in a combined form, preferably in the form of a mixture.

In one embodiment, the invention relates to a concentrate for a dialysis liquid, preferably a dry concentrate, at least comprising an acid and a physiologically acceptable electrolyte, characterized in that the acid comprises at least one acidic ion exchanger or is an acidic ion exchanger, wherein the at least one ion exchanger and the physiologically acceptable electrolyte are provided in a combined form in a container, preferably in the form of a mixture.

The term "container" as used herein encompasses terms such as "packaging" or "bag" or "cartridge". In one embodiment, the term "container" means also a container, which, preferably, may be removed from a dialysis device or a device, which is connected to a dialysis device, and may be reinserted into said device. In a further embodiment, the term "container" means also that said container is accessible for water and/or a physiologically acceptable electrolyte solution, preferably a sodium chloride solution, in order to dissolve the components, which are present in the container, and/or to release protons from them.

In a further embodiment, the concentrate, which preferably is in the form of a dry concentrate, is in a two-part form. In this embodiment, the concentrate comprises or the concentrate consists of two components. In this two-part form, the acidic ion exchanger and the physiologically acceptable electrolyte are separated from one another.

Preferably, then the components of the concentrate are provided in separate containers, packagings or are provided in a container or in a packaging having several compartments, in which, separated from one another, the acidic ion exchanger and the physiologically acceptable electrolyte are provided.

In one embodiment, the invention relates to a concentrate for a dialysis liquid, preferably to a dry concentrate, at least comprising an acid and a physiologically acceptable electrolyte, characterized in that the acid comprises at least one acidic ion exchanger or that the acid is an acidic ion exchanger, wherein the at least one ion exchanger and the physiologically acceptable electrolyte are provided separately from one another, preferably separately from one another in a container, respectively.

In a further embodiment, the acidic ion exchanger and preferably sodium salt may be provided in combined form, and a physiologically acceptable electrolyte, which may comprise one or several of the remaining electrolyte components, also additionally sodium chloride, is provided separately from it; or the acidic ion exchanger and a physiologically acceptable electrolyte may be provided in combined form, and further components of the concentrate or of the physiologically acceptable electrolyte, preferably sodium chloride, are provided separately from it; or the acidic ion exchanger may be provided on its own and a physiologically acceptable electrolyte and further components of the concentrate or of the physiologically acceptable electrolyte, preferably sodium chloride, are provided in combined form.

In one embodiment, the concentrate, preferably the dry concentrate, provides the acidic ion exchanger and sodium chloride in combined form, and a physiologically acceptable electrolyte separately from it. Thus, the acidic ion exchanger and sodium chloride may be provided in one packaging, respectively in one compartment of the packaging, whereas the physiologically acceptable electrolyte is provided in a further packaging, or within the same packaging in another compartment.

In a further embodiment, the concentrate, which preferably is in the form of a dry concentrate, is in a three-part form. In this embodiment, the concentrate comprises three components, or the concentrate consists of three components. In this form, the acidic ion exchanger, a physiologically acceptable electrolyte and further components of the concentrate, or of the physiologically acceptable electrolyte, preferably sodium chloride, are provided separately from one another, respectively. Thus, the acidic ion exchanger, a physiologically acceptable electrolyte and sodium chloride may be provided in a packaging, respectively, or within the same packaging in different compartments.

In one embodiment, the physiologically acceptable electrolyte may comprise further additives, preferably such as glucose.

In a further embodiment, it is also possible to provide the acidic ion exchanger and sodium chloride and the physiologically acceptable electrolyte in a combined form, and a basic buffer substance, preferably sodium hydrogen carbonate, separately from it.

In a further embodiment, the ion exchanger may be regenerated after the use according to the invention and/or after the release of protons. For this, preferably mineral acids such as hydrochloric acid, sulfur acid, nitric acid, or carboxylic acids such as acetic acid, citric acid, or lactic acid may be fed to the ion exchanger, or to the container, preferably the cartridge, which accommodates the ion exchanger.

In a further embodiment according to the first aspect of the invention, the concentrate for the dialysis liquid may not only be provided as a dry concentrate, however, also as liquid concentrate.

In one embodiment, then the concentrate is provided in the form of a liquid concentrate, which comprises water besides the acidic ion exchanger or the physiologically acceptable electrolyte, and preferably additionally sodium chloride and optionally glucose.

Preferred concentrates in form of liquid concentrates contain:
(a) water,
(b) the acidic ion exchanger having an exchange capacity for cations of from 20 mEq/L to 900 mEq/L,
(c) chloride in a concentration of from 1,000 mEq/L to 7,000 mEq/L, preferably of from 1,000 mEq/L to 2,000 mEq/L, and
(d) at least one physiologically acceptable cation and a physiologically acceptable anion.

In one embodiment, the liquid concentrate has a pH value of less than 4.

According to a second aspect, the invention relates to a dialysis liquid, at least comprising a concentrate for a dialysis liquid according to the first aspect or according to one of the embodiments, which are described therein, and water.

As water, preferably osmosis water is used that is typically used in dialysis.

According to a third aspect, the invention relates to a method of making the dialysis liquid according to the second aspect or according to any one of the embodiments, which are described therein, at least comprising step (i):
(i) mixing the concentrate according to the first aspect or one of the embodiments described therein with water.

In a preferred embodiment of the method, the acidic ion exchanger is provided in combined form with the physiologically acceptable electrolyte and sodium chloride in a container, wherein the concentrate preferably is provided as dry concentrate. After addition of water, the protons are released from the ion exchanger due to ion exchange by means of the sodium chloride that is present in the salt portion.

In a further preferred embodiment, the acidic ion exchanger is provided in combined form with sodium chloride in a first container, and the physiologically acceptable electrolyte in a second container. This has the advantage that, when water is added, at first sodium ions reach the acidic ion exchanger and release protons from it, whereas the dibasic cations from the physiologically acceptable electrolytes, which have a higher affinity towards the ion exchanger than the sodium ions from the sodium chloride, which, however, are present in the acid concentrate in relatively low amounts only, are not removed from the solution, and thus are available for dialysis.

In a further preferred embodiment, the acidic ion exchanger is in a container, preferably in a cartridge, in the dialysis device or in a device, which is connected to the dialysis device. A container, preferably a bag, is connected to the dialysis device or to the device that is connected to the dialysis device, which exclusively contains sodium chloride. When water flows through the bag, sodium chloride is released, which is directed into the container, which comprises the acidic ion exchanger, wherein the protons in the acidic ion exchanger are released during the making of the dialysis liquid by means of the aqueous salt solution. This has further the advantage that the cartridge comprising the ion exchanger may be regenerated during the hemodialysis with acid, and thus may be used several times. Preferably, then the physiologically acceptable electrolyte is provided in a form separated from the ion exchanger and from the sodium chloride, preferably at a location in the dialysis device, which is located downstream the cartridge.

Thus, in one embodiment, step (i) comprises at least steps (i') to (i'''), and the method optionally comprises subsequently to step (i) or (i''') step (ii):
(i') inserting a container, preferably a cartridge, in which the at least one ion exchanger is present, into a dialysis device or into a device, which is connected to the dialysis device;
(i'') inserting a container, preferably a bag, which contains sodium chloride, into the dialysis device, or into a device, which is connected to the dialysis device;
(i''') passing water through the container, which has been inserted in step (i'') such that the dissolved sodium chloride gets into the container, which has been inserted in step (i'), and releases in said container protons from the acidic ion exchanger, which are directed into the dialysis device;
(ii) regenerating the ion exchanger, which is obtained after step (i) or (i''').

Preferably, the physiologically acceptable electrolyte is located at a position, which is downstream the container of step (i').

Thus, the invention also relates to a concentrate for a dialysis liquid, preferably a dry concentrate, which comprises an ion exchanger in a container, preferably in a cartridge, wherein the container is arranged in the dialysis device or in a device, which is upstream of said dialysis device, and for the manufacture of the concentrate in the dialysis device or in a device, which is upstream of said dialysis device.

According to a fourth aspect, the invention relates to a dialysis device, at least comprising a concentrate for a dialysis liquid according to the first aspect or one of the embodiments described therein, in particular the embodiment, in which the acidic ion exchanger is provided in a container, wherein the container is inserted in the dialysis device or in a device, which is connected to the dialysis device; or the invention relates to a dialysis device at least comprising a dialysis liquid according to the second aspect.

In one embodiment, the dialysis device further comprises a container for the receiving of sodium chloride, which is in the dialysis device or in a device, which is connected to the dialysis device, wherein, when water passes through the container, dissolved sodium chloride gets into the container that accommodates the acidic ion exchanger, and releases protons from the acidic ion exchanger, which are directed into the dialysis device.

According to a fifth aspect, the invention relates to the use of a method of making a dialysis liquid according to the third aspect for dialysis of blood or in the dialysis of blood.

According to a sixth aspect, the invention relates to the use of a dialysis device according to the fourth aspect or to one of the embodiments described therein, for performing a method according to the third aspect or one of the embodiments described therein.

According to a seventh aspect, the invention relates to the use of an acidic ion exchanger.

According to the invention, the acidic ion exchanger may be used
- in or for dialysis of blood; or
- for making a concentrate for a dialysis liquid, preferably for a concentrate according to the first aspect; or
- for making a dialysis liquid, preferably a dialysis liquid according to the second aspect; or
- for adjusting the pH value in a concentrate for a dialysis liquid, preferably in a concentrate for a dialysis liquid according to the first aspect; or in a dialysis liquid, preferably a dialysis liquid according to the second aspect; or
- in a dialysis device or in a device, which is connected to said dialysis device, preferably in a dialysis device according to the fourth aspect.

EXAMPLE

A dialysis liquid is adjusted by means of an acidic ion exchanger such that it contains 3 mmole protons per liter. The acidic ion exchanger is a commercially available acidic ion exchanger based on a carboxyl group-containing acrylic polymer having a capacity for ion exchange of 3,800 mmole protons per liter (Dowex® MAC-3). 95 ml of the acidic ion exchanger are used per 120 liters of dialysis liquid.

The invention claimed is:

1. A concentrate for a dialysis liquid, the concentrate comprising an acid and a physiologically acceptable electrolyte, characterized in that the acid comprises an acidic ion exchanger, wherein the acidic ion exchanger comprises one or more members selected from the set consisting of sulfonate groups, sulfate groups, phosphate groups, phosphonate groups, and carboxylate groups wherein the groups are bound to a cross-linked polystyrene or poly(meth)acrylate, and wherein the concentrate is provided in a container and the ion exchanger and the physiologically acceptable electrolyte are provided in the form of a mixture in said container, where in the container is accessible to water or a sodium chloride solution, in order to release protons from the acidic ion exchanger.

2. The concentrate according to claim 1, wherein the physiologically acceptable electrolyte comprises one or more cations selected from the set consisting of magnesium, calcium, potassium, and sodium and one or more anions selected from the set consisting of chloride, acetate, and lactate.

3. The concentrate according to claim 1, wherein the concentrate is provided as dry concentrate.

4. A method of making a dialysis liquid comprising at least one concentrate for a dialysis liquid according to claim 1, and water, comprising at least step (i):
 (i) mixing the concentrate according to claim 1 with water.

5. A dialysis device, comprising the concentrate provided in the container according to claim 1, wherein the container is inserted into the dialysis device or into a device which is connected to said dialysis device and wherein the container is accessible to water.

6. The method of claim 4, further comprising, subsequently to step (i), step (ii):
 (ii) regenerating the acidic ion exchanger after the release of protons, which has been obtained after step (i).

7. A method of dialyzing blood, the method comprising at least steps (i) and (ii):
 (i) mixing the concentrate according to claim 1 with water in order to make a dialysis liquid;
 (ii) passing the dialysis liquid made in step (i) through a dialyzer, where it is brought into contact with blood.

* * * * *